(12) United States Patent
Guerrero et al.

(10) Patent No.: US 7,347,345 B2
(45) Date of Patent: Mar. 25, 2008

(54) DEVICE AND METHOD FOR HYGIENICALLY DELIVERING A LIQUID FOOD

(75) Inventors: Arturo F. Guerrero, Warren, CT (US); Balakrishna Reddy, Ridgefield, CT (US); Mark D. Beaumont, New Milford, CT (US); Eric E. Hartman, Ridgefield, CT (US)

(73) Assignee: Nestec S.A., Vevey (CH)

( * ) Notice: Subject to any disclaimer, the term of this patent is extended or adjusted under 35 U.S.C. 154(b) by 570 days.

(21) Appl. No.: 10/860,494

(22) Filed: Jun. 2, 2004

(65) Prior Publication Data

US 2005/0269362 A1 Dec. 8, 2005

(51) Int. Cl.
*B67D 1/08* (2006.01)

(52) U.S. Cl. ............... 222/148; 222/83; 222/129.1; 222/149; 134/168 C; 239/106; 239/112

(58) Field of Classification Search ........... 222/148, 222/129.1, 1, 149, 83; 134/22.12, 166 R, 134/168 C, 22.11; 239/104, 106, 107, 110, 239/112

See application file for complete search history.

(56) References Cited

U.S. PATENT DOCUMENTS

| | | | | |
|---|---|---|---|---|
| 1,261,986 | A * | 4/1918 | White ................. | 222/129.1 |
| 2,653,733 | A * | 9/1953 | Rudd ................. | 222/129.4 |
| 3,152,725 | A | 10/1964 | McCarter ............. | 222/129.4 |
| 3,221,861 | A | 12/1965 | Maxwell ............. | 194/13 |
| 3,764,041 | A * | 10/1973 | Noll .................. | 222/1 |
| 4,200,206 | A * | 4/1980 | Chase et al. .......... | 222/144.5 |
| 4,358,029 | A * | 11/1982 | Yomoda ............... | 222/133 |
| 5,226,565 | A * | 7/1993 | Hladis et al. ......... | 222/148 |
| 5,334,353 | A * | 8/1994 | Blattner ............... | 422/100 |
| 5,525,515 | A * | 6/1996 | Blattner ............... | 436/49 |
| 6,497,155 | B1 * | 12/2002 | Feygin et al. .......... | 73/863.22 |

FOREIGN PATENT DOCUMENTS

| | | |
|---|---|---|
| CH | 653976 | 1/1986 |
| DE | 556223 | 8/1932 |
| DE | 1003068 | 2/1957 |
| DE | 3002100 | 7/1981 |
| DE | 19625922 | 11/1997 |
| EP | 1025917 | 8/2000 |
| GB | 768239 | 2/1957 |
| GB | 2 160 178 A | 12/1985 |
| GB | 2 348 637 A | 10/2000 |
| GB | 2 385 291 A | 8/2003 |
| JP | 7309397 | 11/1995 |

* cited by examiner

*Primary Examiner*—Frederick C. Nicolas
(74) *Attorney, Agent, or Firm*—Bell, Boyd & Lloyd LLP

(57) ABSTRACT

A method and device for hygienically delivering a liquid food to or from a food or beverage dispenser by delivering a flow of liquid food through an outlet positioned at a distance of all surfaces of the dispenser and by frequently cleaning the outlet with a flow of cleaning liquid directed onto the external surfaces demarcating the outlet to eliminate the liquid and solid food residue. The device may include a connection fitment with an elongated food delivery member which is configured to connect to a cleaning chamber of the dispenser. The device can be easier and more conveniently cleaned and/or sanitized enabling the dispensing of microbial sensitive food products such as milk concentrate and the like.

17 Claims, 4 Drawing Sheets

DEVICE AND METHOD FOR HYGIENICALLY DELIVERING A LIQUID FOOD

FIELD OF THE INVENTION

The present invention relates to a method for hygienically delivering a liquid food in a food or beverage dispenser. The invention also relates to a hygienic delivery device adapted for such a method. The invention also relates to a liquid food package adapted to connect to a food or beverage dispenser by means of the hygienic delivery device of the invention.

BACKGROUND

In the foodservice domain, there is a high demand in varied food preparations and beverages dispensed from automatic dispensing systems. In particular, hot and cold specialty beverages such as dairy based beverages are very much appreciated. Popular frothed and non-frothed dairy based beverages encompass, for instance, cappuccino, latte, mocchiato, and coffee frappe. Such beverages are usually produced from powder milk which is mixed with water and delivered simultaneously with or before coffee is delivered in the cup.

However, beverage powder poses a number of disadvantages. In particular, powder is difficult to dissolve in tepid or cold water, and sometimes also, in hot water, precisely, when powder contains an amount of fat such as in whole or semi-skim milk powder or insoluble proteins such as in skim milk powder. Therefore, powder requires more energy and/or time for mixing with other fluids but also for delivering a decent froth on top of the beverage. Powder is also sensitive to humidity and renders dose-to-dose accuracy more difficult to achieve. At certain levels of humidity, the dosing devices, such as canisters and augers, may even be blocked up to an extent which requires intervention from a maintenance operator. Food powder also suffers from a lower image in term of quality and is viewed as inferior in quality compared to liquid food.

Therefore, there is an increasing demand for dispensing systems which can deliver dairy based beverages in a more convenient way, while requiring less maintenance, low energy consumption and while providing frothed or non-frothed beverages of high quality.

Therefore, liquid food proves to offer these important advantages over food powder. However, contrary to food powder, certain liquid foods which are more microbiologically sensitive such as milk based and juices tend to spoil rapidly if drastic hygiene conditions are not respected. When food such as milk based products and juices are contaminated, their sensory quality is affected and it becomes unsafe to consumption with sometimes even risks of food poisoning.

Handling a liquid food product such as liquid milk, milk concentrate or juice in a safe and hygienic way in a dispenser system usually requires maintaining the product in refrigerated conditions when the container is opened in order to slow down microbial growth and extend the shelf life of the product sufficiently to avoid wasting too much product. However, refrigeration does not avoid microbial contamination but simply reduces the bacterial growth at the low temperature. Furthermore, it also requires frequent cleaning operations. To thorough clean the dispenser, it is usually necessary to disassemble parts of the machine. This disassembly is time consuming and labour intensive requiring training for the foodservice operators and increasing the chances for contamination if operators do not follow required hygienic standards or do not use the right tools.

Furthermore, the fitment areas for connection of the source of liquid food with the dispenser offer critical zones for microbial contamination and growth. Indeed, food residue and deposits tend to accumulate and settle in these connection zones and these surfaces are then difficult to be properly sanitized or cleaned. Again, dismantling the connections is often necessary to continue to ensure a high level of safety and food quality in the dispensing service.

GB 2,385,291 A relates to a liquid dispenser for dispensing a beverage comprising a reservoir for storing a liquid that supports microbial growth connected to a delivery outlet that is constructed as a capillary tube positioned to aim a fine jet of liquid directly into a dispensing container. The capillary tube is regularly sterilized by exposing the delivery outlet to an oxidizing gas such as ozone or chlorine dioxide. For that, the capillary tube is enclosed in a clamshell casing during the sterilizing process and the oxidizing gas is circulated around the capillary tube. This solution poses several problems in particular related to the way of sterilizing the capillary tube by the use of an oxidizing gas. Indeed, distributing, forcing the gas around the tube and evacuating the gas require a sophisticated arrangement. The gas is also corrosive and the gas must remain confined to the delivery outlet to avoid chemical attacks to other parts of the machine. The gas has a sterilization effect but does not remove liquid drops or solid residues, which can become a source of contamination and growth. In particular, the system requires repeated mechanical shocks to remove the last droplet of milk at the bottom of the capillary tube. This adds to the complexity and affects the reliability of the system. Furthermore, such system is not well adapted to deliver a food liquid to dispensing components downstream such as a mixing bowl and/or a whipper because of the use of oxidizing gas which can corrode or accelerate the aging of these components.

Therefore, there is a need for handling and delivering liquid food in or from a dispenser while using a simpler and more reliable method for cleaning and sanitizing the parts in contact with the liquid food which are subjected to risks of microbial growth.

There is also a need for a method which does not require dismantling of parts of the dispenser while reducing the risks of microbial spoilage.

There is also a need for providing a safer connection between the source of liquid food and the dispenser.

There is a need for a system that can be operated at any time and as frequently as required by the circumstances and/or safety regulations and without requiring the intervention of a maintenance operator.

There is also a need for a system that can offer an automatic cleaning and a sanitizing solution, which can be more easily controlled and made less susceptible to contamination by operator mishandling. The present invention now satisfies these needs.

SUMMARY OF THE INVENTION

Accordingly, the present invention relates to a hygienic liquid food delivery device for dispensing a liquid food to or from a food or beverage dispenser comprising at least one elongated delivery member for connecting to a liquid food source. The elongated member is tubular to duct the liquid food to an outlet at the tip of the tubular member; and the outlet is configured for dispensing the liquid food to or from the dispenser with the outlet of the elongated delivery member being positionable in a delivery position at distance of all surfaces of the dispenser. The device also includes at least one cleaning liquid distribution conduit with at least one outlet directed toward the elongated delivery member and configured to dispense a cleaning liquid at least onto the surface of the tip of the delivery member.

The use of a cleaning liquid which is dispensed onto the surface of the elongated liquid delivery member cleans the critical parts of the member by washing any remaining liquid droplet or solid residue from these parts. As a result, there is no need for a mechanical or piezoelectric vibrating device for physically dislodging the droplet. The liquid food droplet can be physically washed as a result of the velocity of the cleaning liquid dispensed at the tip of the elongated liquid delivery member and/or be diluted by the cleaning liquid and be drained in or out of the dispenser. The device is also much simpler as compared to an oxidizing gas generator which is usually coupled to a system for collecting the gas or depleting it before it can safely be released to atmosphere.

In a preferred aspect of the invention, the cleaning liquid distribution conduit is connected to a source of hot water to distribute hot water as the preferred cleaning liquid onto the surface of the needle. Hot water is the preferred cleaning liquid for washing the needle since it can be produced easily and can be drained without significant risk for the environment. As many food or beverage dispensers usually enclose a water heater such as a boiler, a thermoblock or an instant heater, the cleaning fluid can be easily produced on-demand and in an inexpensive way for frequent cleaning thus offering more opportunity to equip the dispenser with the delivery of microbial sensitive food liquids such as milk or milk concentrate and the like. When used as the cleaning fluid, hot water must usually be heated at a temperature of at least 65° C. in order to also provide a sanitizing effect that kills the microorganisms. The sanitizing effect with only hot water may not necessarily be sufficient to kill all heat resistant microorganisms such as spores and the like, but the flow of the liquid fluid during washing enables to reduce the number of microorganisms to levels considered as safe by dislodging these microorganisms and spores to avoid the formation of colonies to grow at the critical dispensing region.

The cleaning liquid distribution conduit can also be connected to a source of liquid detergent. The liquid detergent may have a simple cleaning effect or may have a combined cleaning and bactericidal effect. Water by itself can be used as cleaning/sanitizing solution, especially hot water. Detergent/sanitizing solution can also be injected into the water stream, as water runs to the hygienic chamber, for better cleaning or sanitation, which becomes more important if cold or ambient water is used instead of hot water.

Therefore, the use of liquid detergent in combination with water also permits the use of cold or ambient temperature water instead of hot water for cleaning and or sanitation.

The conduit may also be connected both to a source of detergent solution and to a source of water; hot or cold or ambient water, and a control and valve means can be provided to control the selective dispense of detergent solution and water at periodical intervals to ensure the tip of the needle is well cleaned and sanitized. The valve means may include a three-way valve or similar valve means.

BRIEF DESCRIPTION OF THE DRAWING

Preferred embodiments of the invention are now presented in the following detailed description when considered in conjunction with the appended drawings figures, wherein.

DETAILED DESCRIPTION OF THE PREFERRED EMBODIMENTS

Figure 1:
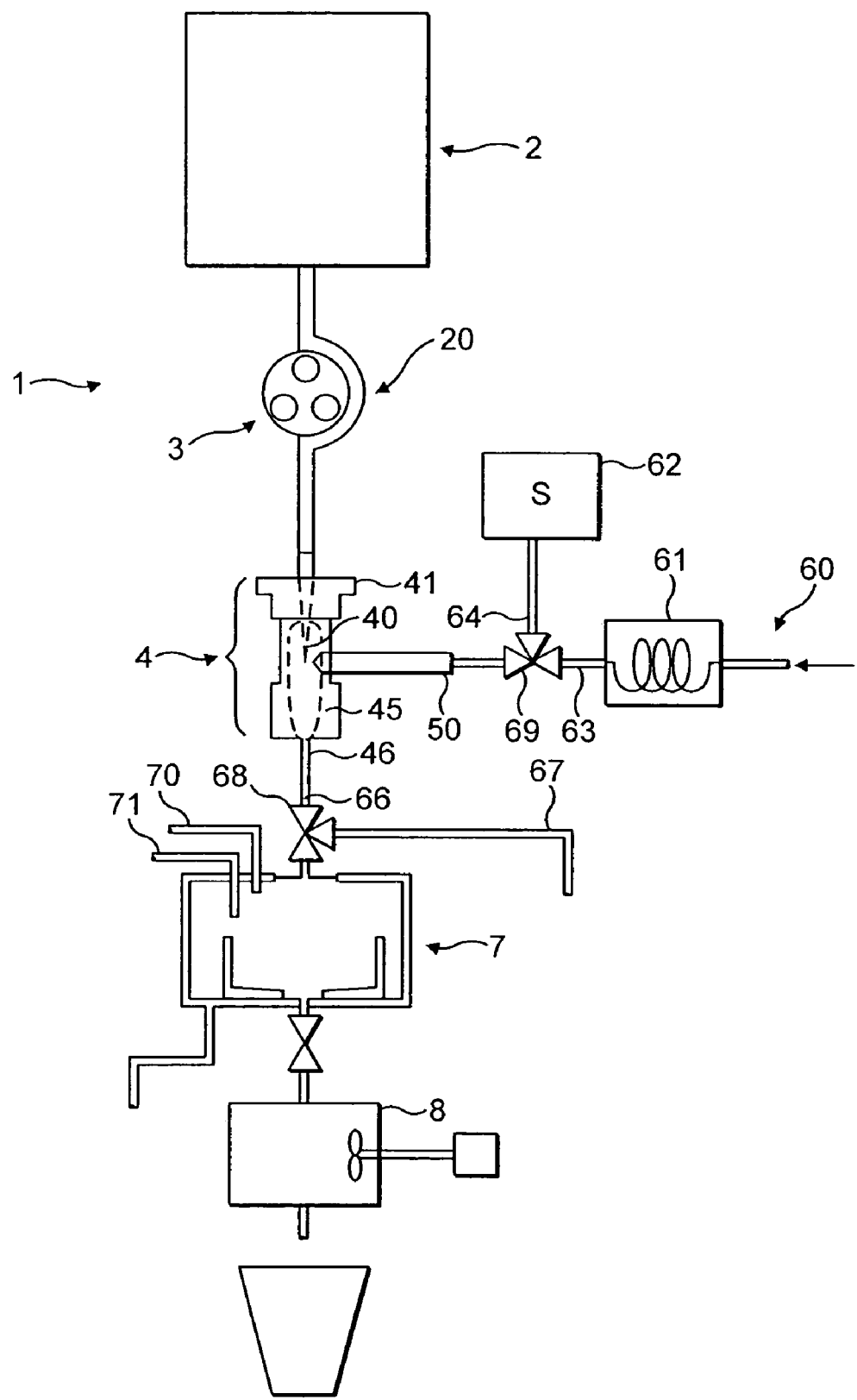
FIG. 1 is a perspective, exposed view of a dispenser according to the invention.

In one preferred of the invention, a cleaning chamber is provided. The chamber comprises a passage for the elongated liquid delivery member to be inserted therein with the outlet of the elongated liquid delivery member being maintained at distance from the inside surfaces of the chamber. The chamber also comprises at least one outlet configured for dispensing the liquid food to or from the dispenser. Thus, the chamber maintains a confined area under cleaning and/or sanitizing control. The chamber also prevents splashing of liquid food outside of the dispenser and/or on surfaces of the dispenser that cannot be automatically cleaned or rinsed. The same water used for cleaning can be blended with a liquid food in a final preparation.

The outlet of the chamber enables to funnel the liquid food into components of the dispenser such as a dispensing or mixing conduit, a mixing bowl, a whipper or, alternatively, into the beverage or food container directly.

In another aspect of the invention, the at least one cleaning liquid distribution conduit leads to the inside of the chamber. The conduit ends by at least a nozzle which is configured to dispense a spray of cleaning liquid in a diffuse manner so that the cleaning liquid also impacts on the inside surfaces of the chamber. Therefore, the inside of the chamber can be frequently cleaned and/or sanitized at the same time as the whole part of the elongated delivery member which protrudes in the chamber.

It can be noted that the number of conduits is not limited. For instance, one conduit may be provided for cleaning the elongated delivery member with a jet which impacts precisely in directional manner on the delivery member at a sufficient velocity and one conduit may be provided with a spraying effect to clean the surface of the chamber in a more diffuse manner.

In another preferred embodiment, the conduit for cleaning the elongated delivery member and for cleaning the chamber is the same conduit. For that the chamber is traversed by a single conduit which delivers a spray of cleaning liquid both on the deliver member's tip and onto the inside surfaces of the chamber.

In yet another embodiment, the nozzle has a conical, spherical or square end with a plurality of holes formed through the surface of the nozzle to deliver a spray of cleaning liquid. Although other shapes can be envisaged, the end of the nozzle is preferably conical to diffuse the cleaning liquid in many different directions and at different angles.

The nozzle may also have other types of outlet for delivering a spray of liquid such as at least one slit and/or one small restriction. The spray nozzle is such that it divides the flow of cleaning liquid in a sprinkle configuration and so it optimizes contact with the inside surfaces of the chamber and the surface of the elongated delivery member which enters the chamber.

In an alternative embodiment, the at least one elongated delivery member is configured in the chamber to aim a jet of liquid food directly through the outlet of the chamber. The jet of liquid is preferably a thin jet which is directed at a relatively high velocity in the center of the outlet of the chamber. This participates to the reduction of the risk of side splashing and so it maintains the liquid and/or solid food projections on the surfaces of the chamber at a minimum although all projections cannot be fully avoided in practice.

In another embodiment, the at least one elongated liquid delivery member is positioned to aim a jet of liquid food directly into the dispensing container.

In another aspect of the invention, the elongated liquid delivery member is a part of a connection fitment comprising a body with a liquid inlet for receiving the food liquid. The connection fitment is configured to be inserted in the chamber and be retained in the chamber by connection means when the elongated liquid delivery member is positioned in place within the chamber.

The elongated liquid delivery member is thus preferably a hollow needle adapted to duct the liquid food therethrough and deliver it in a relatively precise linear direction. The relatively small exposed surfaces of the needle enables to considerably reduce the risk of microbial growth and is consequently easier to clean and/or sanitized. The needle configuration also offers more convenient, hygienic and quicker modes of assembly with the chamber or dispenser.

The connection fitment further comprises a protective member attached to the body which is configured to keep the needle clean before the first use.

The protective member preferably includes a collapsible portion that functions like a bellow which is configured to surround the needle to protect it and to collapse as the needle is inserted in the chamber so to allow the needle to puncture the protective member to uncover at least the outlet of the needle in the chamber.

This protective member may end by a septum which can be made of various puncturable material such as paper, plastic membrane or thin rubber. The septum may be an integral part of this protective member or be a distinct part which secures to the collapsible portion of the protective member.

In a particular embodiment, the collapsible portion, that functions as a bellow, has an enlargement with a section larger than the passage of the chamber which engages the edges of the passage of the chamber as the needle is inserted in the chamber causing the collapsible portion to collapse and the needle to puncture the septum. This construction enables a rapid connection and ensures that the needle is properly uncovered when it is inserted in the chamber.

The protective member for the needle may be attached to the body of the fitment by any suitable connection means. In a preferred embodiment, a ring is snapped on the circumferential edge of the body.

As further protective means, the connection fitment can be protected by a tamper evidence rigid cover which overlaps the bellow. This cover prevents from any premature collapsing and puncturing of the protective member and maintains the needle clean before the first food delivery. The tamper evidence cover may be connected to the body of the connection fitment by any suitable tamper evidence connection means. Preferably, the tamper evidence connection cover comprises a ring which is secured in a circumferential groove of the body of the fitment and a tubular extension portion covering the bellow; the extension portion being secured in cleavable manner to the ring.

The invention also relates to a food liquid package comprising a container with liquid food, a tube connected by one end to the container and by the other end to a connection fitment as aforementioned.

The invention also relates to a method for hygienically delivering a liquid food to or from a food or beverage dispenser by delivering a flow of liquid food from an outlet which is positioned at a distance of all surfaces of the dispenser and by frequently cleaning with a cleaning liquid the external surfaces demarcating the outlet to eliminate the liquid and solid food residue on the surfaces.

Preferably, the cleaning liquid comprises hot water. Hot water may preferably be heated to within a temperature range having a sanitation effect. The cleaning fluid may also be cold or ambient water. The outlet preferably protrudes from a needle inserted in a chamber whose surfaces are also cleaned by the cleaning fluid. The chamber ensures the control of a confined cleaning area whereas the outlet is maintained distant from the surfaces of the chamber. The same water used for cleaning and sanitation can be blended with the liquid food in a separate element subsequent to the cleaning chamber. The water used for cleaning can be forced to a drain or collection container if blending with the liquid food is not desired.

The outlet is preferably maintained distant from the surfaces by a hollow needle whose tip demarcates the outlet. The configuration of a needle ensures a more laminar flow of the liquid food delivered and, therefore, favors the control of the flow for a cleaner delivery by reducing projections of liquid on the side surfaces of the dispenser.

The flow of cleaning fluid is sent from a zone at distance from the outlet of the needle. For example, the cleaning fluid can be sent from one or more nozzles which are directed toward the outlet but kept distant from the outlet of the needle.

In order to provide an extensive cleaning area around the outlet, the cleaning fluid is dispensed in the form of at least one spray. Therefore, not only the outlet is cleaned and eventually sanitized but also the vicinity of the outlet liquid food which can potentially have spoiled.

The configuration of a needle provides the main advantage to enable the delivery of a non-splashing flow of liquid food in or from the dispenser. Therefore, the liquid can better be funnelled and the projections of liquid are reduced. The needle also provides an improved liquid dosing accuracy and delivers a liquid under velocity which can favor, in certain circumstances the mixing of the liquid food with a diluent and eventually also, when desired, the production of a foam.

In the method of the invention, the flow of liquid food and the flow of cleaning liquid can be synchronized so that cleaning takes place at the required moments. For instance, the flow of cleaning liquid can be programmed to occur before, during of after the dispensing of the liquid food. In one possible way, the water used for cleaning is blended with the liquid food as part of the final product. For instance, the liquid food delivery sequence and the water delivery sequence overlap with the water sequence running longer to clean the system at each food product's reconstitution cycle. The cleaning liquid delivery sequence may also take place a few seconds or minutes after the product reconstitution cycle; in which case the cleaning liquid is drained or collected into a separate container without blending with the final food product.

The present invention is intended to allow an hygienic delivery of a liquid food through a beverage and/or food dispenser. By "hygienic delivery", it is meant that the delivery of liquid food is carried out in a manner which avoids the risks of growth of microorganisms along the path of food in the dispenser. The device should also preferably comply with the international and national regulations in matter of food handling. The term "liquid food" includes anything edible in a non-solid form that can be pumped, expelled under pressure or dispensed by gravity including but not limited to beverages, toppings, soy products, dairy and non-dairy products, culinary and the like. The present invention is well suited for hygienically delivering microorganism sensitive liquid food which can be liquid milk, milk concentrate, non-dairy creamer, cocoa based or coffee based concentrates such as latte or cappuccino concentrates. The liquid food may be stored in refrigerated conditions or shelf stable conditions depending upon the package format, the nature of the food and the desired final food or beverage product to serve.

By reference to FIG. 1, a beverage dispenser 1 is illustrated which comprises a source of bacterial sensitive liquid food such as juice, soy based products, a milk based product, milk or milk concentrate, a mix of non-dairy creamer and liquid coffee or cocoa, or others. The source of liquid food can be stored in a container such as a collapsible pouch 2. Other sorts of containers could also be envisaged such as plastic bottles or metal cans. The pouch offers the advantage to collapse as its contents leaves the inside of the pouch therefore avoiding air to enter the package. The pouch can be supported in a cardboard box to facilitate its shipping, positioning in the dispenser and handling during change over. The package 2 is coupled through a suitable flexible tube 20 via an interface fitment (not shown) to transport the liquid food in or through the dispenser. It can be noted that the package can be remotely located with respect to the dispenser itself or can be stored in the dispenser itself. A pumping mechanism 3 is provided to volumetrically transport and meter the liquid food through the tube. Such pumping mechanism can be a peristaltic pump or any other suitable pump where direct mechanical contact with the liquid food is avoided. In certain circumstances, in particular, for low viscosity liquids, the liquid food can be delivered by simple gravity and the use of a pump is not necessary. A simple pinch valve can be provided along the tube path to open and shut off the liquid delivery. The valve can thus be actuated by a solenoid or similar controlled actuation systems.

The source of liquid food is connected via the tube to a hygienic delivery device 4 of the invention which ensures the cleaning of delivery parts of the liquid food to the downstream region of the dispenser. The device 4 is based on the principle of delivering a liquid from an elongated liquid delivery member 40 attached to the end of the tube 20; member which can be cleaned on a frequent basis by a cleaning liquid projected onto the surface of the member. The outlet of elongated delivery member 40 is positioned at a distance of all surfaces of the dispenser to reduce the extensive spoilage of the surfaces of the dispenser. The elongated delivery member is supported by a body 41 which connects to the chamber 45. The body can be disposable together with the elongated delivery member 40. The package 2, tube 20, elongated delivery member 40 and body 41 are preferably thought as a package assembly which is used only for the time of the delivery of the liquid food and then disposed or recycled. The elongated delivery member is preferably a needle which has a piercing apertured tip. However, the elongated delivery member does not necessarily require a piercing tip. The elongated delivery member can be a thin cylindrical, conical or truncated stem of possible different lengths. Actually, the elongated delivery member external section could be of any other shapes. The elongated delivery member could end by a flat or blunt tip although a piercing tip is preferred in the embodiments which will be described later on. The delivery member has preferably a ratio length-to-mean external longer transverse dimension (e.g., external diameter) which is of at least 5:1, more preferably 8:1 and even more preferably between 10:1 to 50:1. One function of the elongated delivery member 40 is to be able to deliver a jet of liquid in order to better control a clean delivery of the liquid. The elongated delivery member also enables to reduces the external cleaning surfaces and therefore offers less grip to microbial growth. The elongated delivery member also maintains a higher distance between it and the other surfaces of the dispenser which consequently reduces the microbial contamination and growth as well.

The elongated delivery member 40 provides the advantage that it reduces splashing of the liquid food by creating a unidirectional flow under the form of a thin jet. The flow characteristics of the elongated delivery member are typically dependent, among other things, on the diameter/length ratio of the channel and the characteristics of the fluid. For instance, the diameter/length ratio is preferably of from 0.01 to 0.03. A two high diameter ratio will provide a spray effect creating a problem of splashing. The internal diameter of the channel, at the outlet, is preferably of from 0.5 to 3.5 mm, more preferably 1.5 to 3 mm. The internal diameter at the inlet of the elongated delivery member may be larger, for instance, of from 2 to 9 mm, preferably of from 5 to 9 mm and reducing progressively toward the outlet. The outlet may be elliptical to provide a sharper tip or be round.

The needle does not require to be vibrated for droplets of liquid to be shaken off. The cleaning fluid impacting on the surface of the elongated member is usually sufficient to dislodge droplets of liquids at the tip of the needle.

The needle is preferably inserted in a chamber 45 which has an enlarged section, compared to the liquid food delivery tube 20, that enables to maintain the surfaces a sufficient distance away from the tip of the elongated delivery member 40 which comprises the outlet. The chamber 45 is traversed by at least one cleaning liquid distribution conduit 50 with at least one outlet directed toward the elongated delivery member and configured to dispense a cleaning liquid onto the surface the elongated delivery member. The cleaning distribution conduit 50 is connected to at least one source of cleaning liquid. As illustrated in FIG. 1, the source of cleaning fluid can be a hot water supply 60. The hot water supply 60 is produced by heating water through a heater 61. The heater may be any suitable heater generally used in the known beverage or food dispensers such as a boiler, a thermoblock or an instant cartridge heater. The water may come from a water reservoir which is regularly filled or, alternatively, from a direct tap water domestic supply. Cleaning conditions of hot water depend on the nature of the liquid food which is delivered. For milk or milk concentrate and similar highly microbiologically sensitive food, hot water must be heated to a temperature of at least 65° C., preferably of from 75 to 95° C., most preferably of from 80 to 85° C.

The cleaning fluid can encompass the use of a liquid detergent. The detergent may have a simple cleaning effect with an effect on the removal of solids such as fat and proteins or may also have a sanitizing effect on microorganisms. The liquid detergent may be contained in a container 62 to deliver the cleaning solution to the cleaning distribution conduit 50. In that case, the conduit 50 is both connected to the hot water line 63 and detergent line 64 and a control valve 69 is provided to selectively dispense the cleaning solutions to the conduit 50. The control valve can be a three way-valve which is monitored by a central controller of the dispenser (not shown). When a detergent is used, it is important to be able to rinse the elongated delivery member, the chamber and the downstream part of the dispense with water whether hot or ambient. For that, after each cleaning cycle with the detergent, a rinsing cycle with water is carried out to send water through the hygienic delivery device 4 to remove any trace of detergent before any liquid food is again dispensed through the system.

The downstream region of the dispenser is in fluid communication with the hygienic delivery device by a dispensing fluid line 66. The parts can typically comprise a mixing bowl 7 connected downstream to a whipper 8 for foaming liquids on demand. In another arrangement, the mixing bowl can be eliminated and the connection is directly to the whipper. The mixing bowl or the whipper may receive other liquid and/or powder food from food lines 70, 71. The other food products may be, for instance, any food products such as coffee, cocoa, or tea liquid concentrate or powder. The food lines 70, 71 may also be connected upstream to hygienic food delivery devices similar to the one 4 for delivering other microbial sensitive liquid products.

It can be noted that in a more compact and simplified dispensing and cleaning arrangement, the mixing bowl 7 may also serve as the chamber for the hygienic delivery device without departing from the scope of the present invention. However, one advantage of having separate chambers; one chamber for the hygienic delivery device and one chamber for the mixing bowl lies in the possibility offered to drain the cleaning solution from the chamber of the hygienic delivery device directly to a drain line 67 without having to distribute the cleaning solution to the mixing bowl. For this, a three-way valve 68 can control the cleaning paths along a short path through a drain 67 or a longer path through the mixing bowl 7. The short cleaning path may be chosen for more frequent cleaning, for example, after each dispensing cycle in liquid food and the long path for lesser frequent cleaning.

Figure 2:
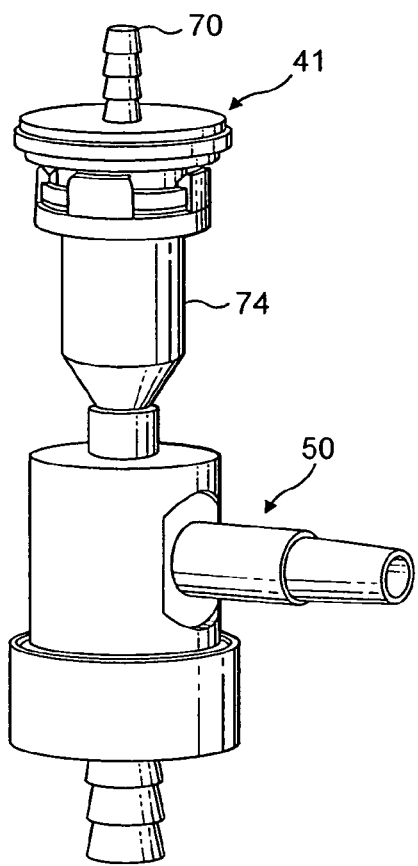
FIG. 2 is a perspective view of a hygienic delivery device of the invention.
Figure 3:
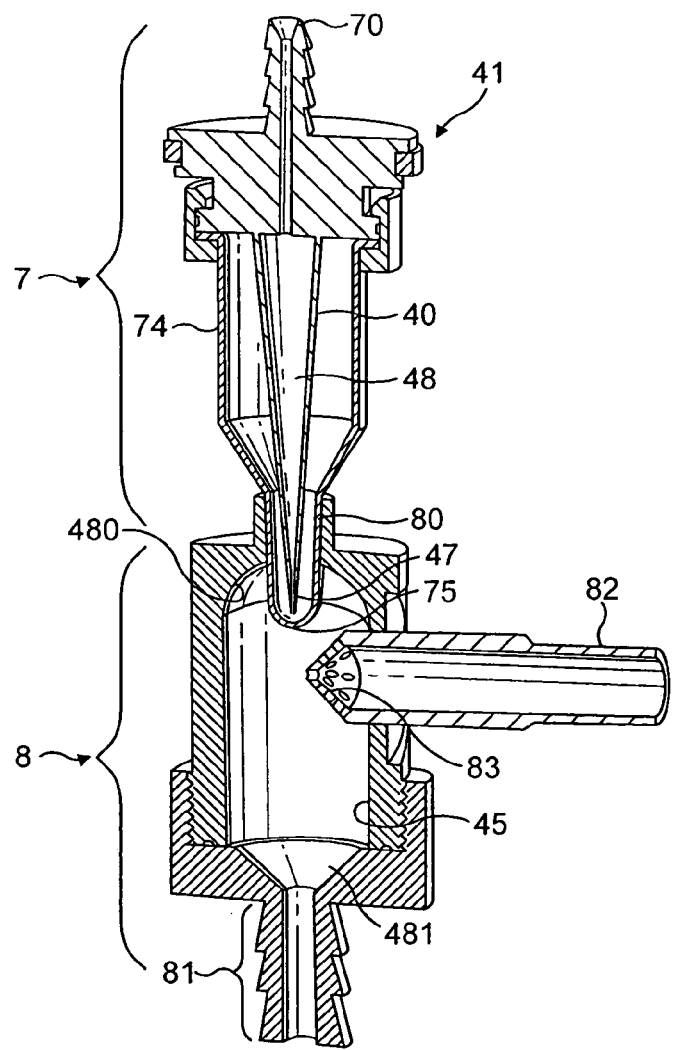
FIG. 3 is a cross-sectional view of the hygienic delivery device of FIG. 2.
Figure 4:
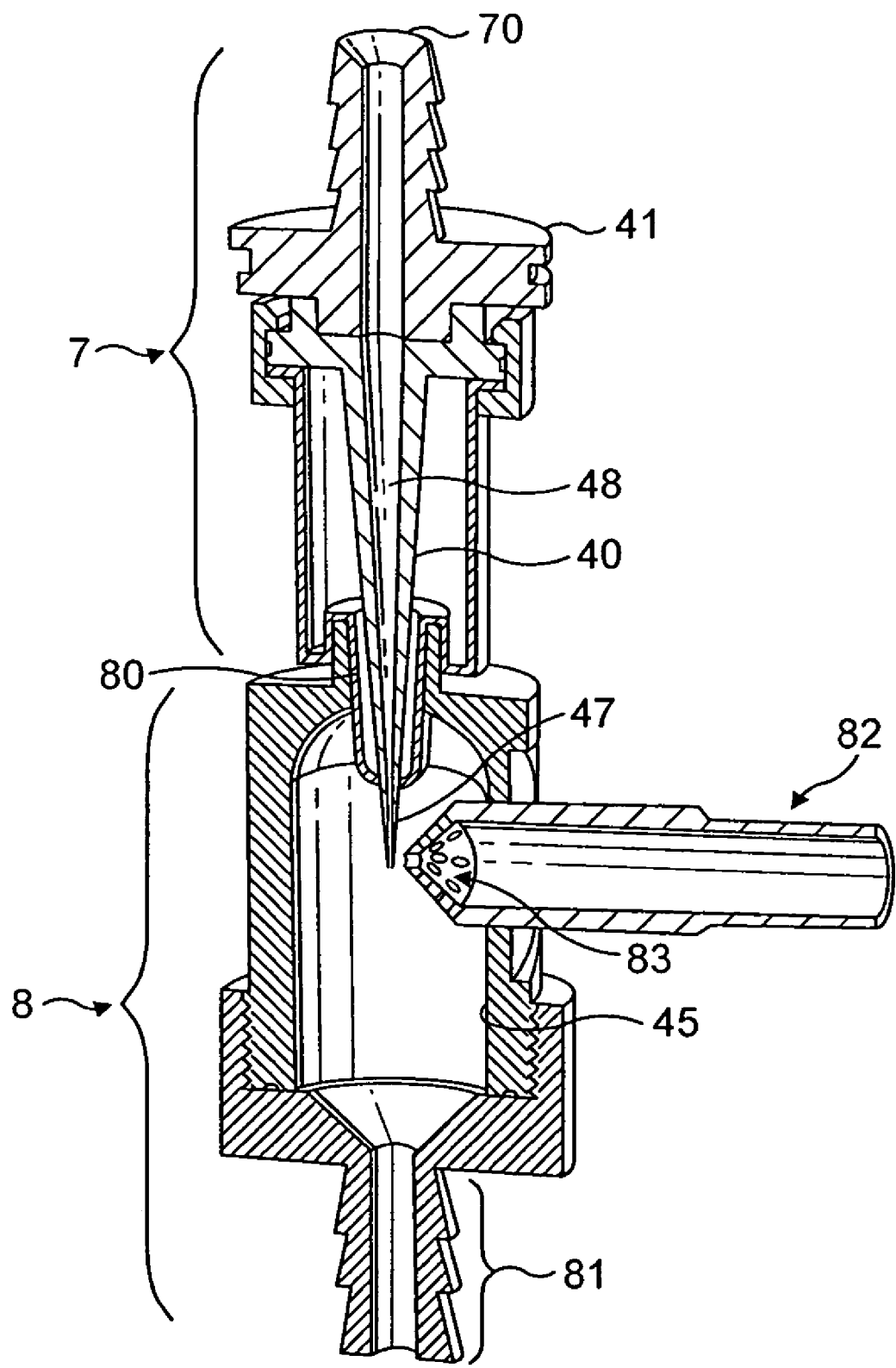
FIG. 4 is another cross-sectional view of the hygienic delivery device of FIG. 2.

FIGS. 2 to 4 refer to a preferred embodiment of the hygienic delivery device which can be installed in, be a part of, or for retrofitting any possible beverage or food dispensers having to handle liquid food and requiring frequent cleaning. The device is thought as a hygienic connection device for connecting a source of liquid food to a food and/or beverage dispenser. The device comprises a connection fitment 7 and a cleaning connection chamber 8 which connect together to establish liquid food communication between the source of liquid food and the dispenser.

The connection fitment comprises an inlet 70 for the food liquid to enter the fitment, a body 41 and at least one elongated delivery member 40 with an apertured piercing tip 47. The elongated delivery member is preferably a needle which is traversed by a longitudinal channel 48. The channel can be of thin capillary diameter or of slightly larger diameter. The channel is preferably cylindrical to guarantee a better closing.

The cleaning connection chamber 8 comprises a passage 80 configured to enable the needle to be inserted in the chamber without the tip of the needle touching the inside of the chamber 45 itself. An outlet portion 81 is provided in the chamber to deliver the liquid food in or from the dispenser. The outlet portion may be configured as a connection gland to connect the cleaning connection portion to a tubing or other components of the dispenser. The cleaning connection chamber 8 is traversed by at least one cleaning conduit 82 for feeding the chamber with a cleaning liquid. The cleaning conduit is positioned to direct a flow of cleaning liquid, at least, toward the tip of the needle. For this, the conduit ends in the chamber by a nozzle 83 which is proximate to the tip of the needle but not touching with the needle.

The nozzle is a spray nozzle configured to form a spray or shower of cleaning liquid which diverges and impacts not only on the tip of the needle but also on an extensive part of the surfaces of the chamber. In a possible embodiment, the nozzle is traversed by a plurality of holes. The holes should be of sufficiently numerous and of small section to confer a diffused spray but of relatively high velocity to dislodge the liquid droplets and possibly solids residue both on the needle and surfaces of the chamber touched by projections of the liquid food. The form of the nozzle can also be important to ensure that the spray diffuses cleaning liquid along a large angular path and so that, consequently, all the surfaces of the chamber are properly washed.

Preferably, the spray nozzle is configured to spray cleaning liquid at an angle of diffusion, at least of about 120 degrees, preferably at about 180 degrees. For this, the nozzle has preferably a conical shape with the plurality of holes being provided through the surface of the cone. The number of holes can be variable. In a preferred mode, the number of holes is within a range of 1 to 50. The diameter of the holes is preferably below 1 mm. The spray nozzle could have other possible configuration like be at least one slit and/or restriction.

For improving the cleaning efficiency, the cleaning liquid distribution conduit 82 is preferably oriented to merge with the chamber along an axis substantially transverse to the longitudinal axis of the needle. However, other orientations can be envisaged such as a conduit which is oriented with an inclination of less than 90 degrees or which is parallel to the needle axis. The number of conduits is also not limited. Also, conduits may be configured to direct a linear jet as opposed to a spraying jet. For instance, linear jets may be oriented to a particular point or edge of the chamber and/or needle which can be particularly critical, for example, at the intersection between the needle and the chamber or at the needle tip.

The shape of the chamber may also be of importance to reduce the areas where food can form a deposit. For example, sharp edges or acute angles in the chamber are preferably avoided. A preferred shape for the chamber is a longitudinal cylindrical inside. The chamber is also preferably positioned in a vertical orientation of the cylinder, or other shapes, with the needle passage 80 facing upward and the food outlet 81 facing downward to favor liquid draining through the chamber. The passage 80 and outlet 81 can also merge with the chamber by portions of progressively widening zones 480, 481 to offer less grip to solid deposit and favor liquid flowing out of the chamber. The zones may be rounded zones or conical zones.

The needle 40 of the fitment connection is preferably protected by a protective member 74 which is at least partially flexible to be punctured by the needle when connection with the cleaning connection chamber 8 is achieved.

The protective member preferably comprises a collapsible rubber or plastic portion of sleeve 740 which surrounds the needle in an impervious manner and connects to the body 41. The protective member comprises a septum 75 which is the region which is pierced by the needle. The septum can be formed of the same material as the collapsible portion 740 such as of rubber, plastic and the like. It may also be formed of a separate piece made of paper, cardboard, rubber or plastic. The base of the protective member is preferably attached to the body by a locking ring 76 snapped on a circumferential protruding edge 77 of the body 41. More particularly, the locking ring 76 comprises a shoulder portion which engages a flange of the protective member and an elastic locking portion which engages by snap-fitting in a circumferential inner groove of the body. This type of connection simplifies the assembly of the device on the production line while it confers a relatively tight and secured protection of the needle.

Other various designs and connection modes of the protective member to the body are possible. The ring may also be attached by screwing or by a permanent mode of attachment. The protective member may also be secured directly to the body by a permanent mode of attachment such as by welding or by an adhesive.

Figure 5:
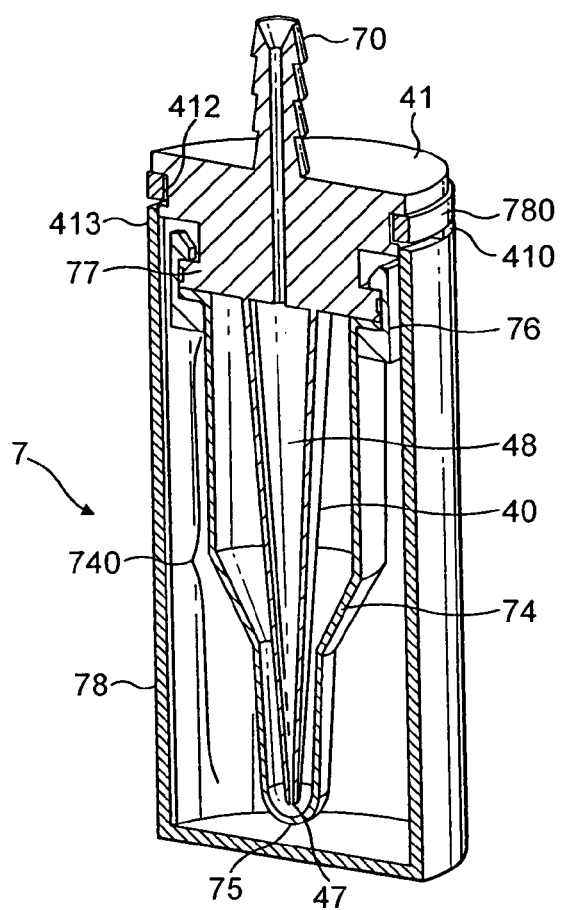
FIG. 5 is a cross-sectional view of a tamper evident connection fitment for use in conjunction with the hygienic delivery device of the invention.

The connection fitment 7 as illustrated in FIG. 5 can be further protected by a tamper evidence system. For this, a tamper evidence cover 78, preferably in rigid plastic material overlaps the protective member 74 and is also secured to the body in a circumferential groove of the body. More particularly, the cover comprises a ring 780 which is secured in an outer groove 412 of the body and comprises a tubular extension portion which covers the protective member. The extension portion 413 is secured in a cleavable manner to the ring such as by one or more small cleavable portions 410 of plastic linking the portion 413 to the ring 412.

After the cover 78 is removed, the connection fitment 7 can be connected to a liquid food package in a removable or non-removable manner. For liquid food for which it is important to respect sterile or quasi-sterile conditions before the first use, the connection fitment should preferably be permanently attached to the rest of the package; i.e., via its tube, The permanent connection can be heat welding, gluing or ultrasonic sealing.

Sterile or quasi-sterile conditions can be produced, for example by heat treating or irradiating the assembly formed by the food package and the connection fitment 7.

Figure 6:
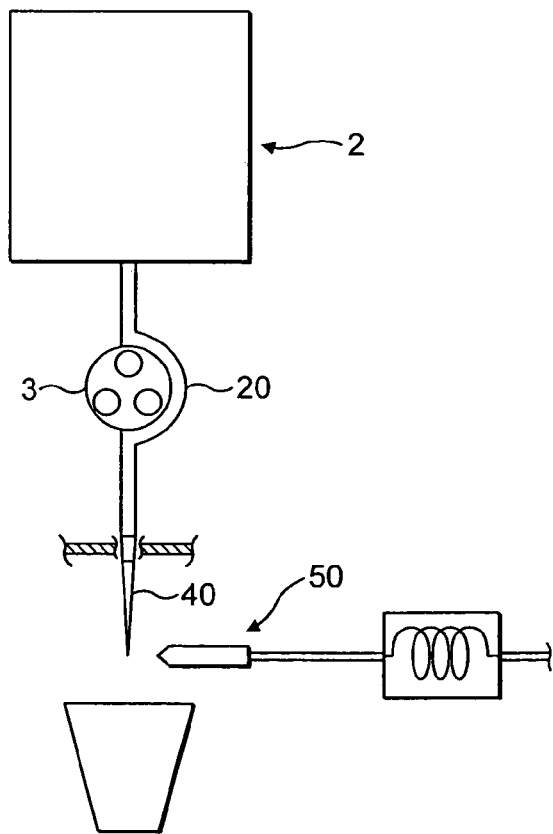
FIG. 6 is a schematic view of another embodiment of the dispenser of the invention.

FIG. 6 shows another embodiment of the invention in which the elongated delivery member 40 is connected on its end base to the liquid food tubing 20 and is positioned to aim a jet of liquid food directly into the dispensing container. A cleaning liquid distribution conduit 50 is directed toward the needle tip in order to regularly clean the needle and maintain a safe degree of hygiene and sanitation at the surface of the needle by avoiding microorganism growth. In this embodiment, a chamber may not be necessary.

In this embodiment, the preferred cleaning liquid is water, and preferable hot water. The cleaning liquid can also contain a detergent or sanitizing agent. The cleaning cycles are run at periodical intervals or in synchronization with the product dispensing. The cleaning liquid may be collected by a drip tray or any suitable collectable means or directed to the drain. The dispensing container may also serve as a collector for the cleaning liquid when this liquid is water used to be blended with a liquid food. In particular, when a beverage or food product is dispensed, hot water can be cycled within a few seconds after the food liquid dispensing time to clean the needle. When the dispenser is not operated during a certain period of time, the conduit 50 can flush hot water at predetermined periods, for instance, every two to 6 hours, to prevent microbial growth at the needle. Filtered or treated water at ambient or cold temperatures can also be used as the cleaning fluid. Water can be used to rinse the needle when the cleaning liquid uses detergent products.

While illustrative embodiments of the invention are disclosed herein, it will be appreciated that numerous modifications and other embodiments may be devised by those skilled in the art. Therefore, it will be understood that the appended claims are intended to cover all such modifications and embodiments that come within the scope of the present invention.

What is claimed is:

1. A hygienic liquid food delivery device for dispensing a liquid food to or from a food or beverage dispenser, the delivery device comprising:
   at least one elongated delivery member for connecting to a liquid food source, the elongated member being tubular to duct the liquid food to an outlet at a tip of the delivery member, the outlet being configured for dispensing the liquid food to or from the dispenser with the outlet of the elongated delivery member being positionable in a delivery position at a distance of all surfaces of the dispenser;
   at least one cleaning liquid distribution conduit with at least one outlet directed toward the elongated delivery member and configured to dispense a cleaning liquid at least onto a surface of the tip of the elongated delivery member; and
   a cleaning chamber comprising a passage for receiving the elongated delivery member therein with the tip of the elongated delivery member being positioned in the delivery position at a spaced distance from inner surfaces of the chamber, wherein the chamber comprises at least one outlet configured for dispensing the liquid food to or from the dispenser.

2. The device according to claim 1, wherein the cleaning liquid distribution conduit is connected to a source of ambient, cold or hot water to distribute water as the cleaning liquid onto a surface of a needle.

3. The device according to claim 1, wherein the cleaning liquid distribution conduit is connected to a source of detergent or sanitizing solution.

4. The device according to claim 1, wherein the at least one cleaning liquid distribution conduit leads to a chamber interior.

5. The device according to claim 4, wherein the cleaning distribution conduit comprises at least one nozzle configured for delivering a spray of the cleaning liquid in a diffuse manner so that the cleaning liquid also impacts on the inner surfaces of the chamber.

6. The device according to claim 5, wherein the conduit for cleaning the tip of the elongated delivery member and for cleaning the surfaces of the chamber are configured as a single conduit.

7. The device according to claim 1, wherein the at least one elongated delivery member is configured in the chamber to deliver a jet of the liquid food directly through the outlet of the chamber.

8. The device according to claim 1, wherein the at least one elongated delivery member is positioned to deliver a jet of the liquid food directly into a dispensing container.

9. The device according to claim 1, wherein the elongated delivery member is a part of a connection fitment comprising a body with a liquid inlet for receiving the food liquid; with the connection fitment being configured to connect to the cleaning chamber.

10. The device according to claim 1, wherein the elongated delivery member is a hollow needle.

11. A hygienic liquid food delivery device for dispensing a liquid food to or from a food or beverage dispenser, the delivery device comprising:
   at least one elongated delivery member for connecting to a liquid food source, the elongated member being tubular to duct the liquid food to an outlet at a tip of the delivery member, the outlet being configured for dispensing the liquid food to or from the dispenser with the outlet of the elongated delivery member being positionable in a delivery position at a distance of all surfaces of the dispenser;
   at least one cleaning liquid distribution conduit with at least one outlet directed toward the elongated delivery member and configured to dispense a cleaning liquid at least onto a surface of the tip of the elongated delivery member; and
   a cleaning chamber comprising a passage for receiving the elongated delivery member therein with the tip of the elongated delivery member being positioned in the delivery position at a spaced distance from inner surfaces of the chamber, wherein the at least one cleaning liquid distribution conduit leads to the chamber interior, wherein the cleaning distribution conduit comprises at least one nozzle configured for delivering a spray of cleaning liquid in a diffuse manner so that the cleaning liquid also impacts on inner surfaces of the chamber and wherein the nozzle has a dispensing end that includes a plurality of holes formed therein.

12. A hygienic liquid food delivery device for dispensing a liquid food to or from a food or beverage dispenser, the delivery device comprising:
   at least one elongated delivery member for connecting to a liquid food source, the elongated member being tubular to duct the liquid food to an outlet at a tip of the delivery member, the outlet being configured for dispensing the liquid food to or from the dispenser with the outlet of the elongated delivery member being positionable in a delivery position at a distance of all surfaces of the dispenser;
   at least one cleaning liquid distribution conduit with at least one outlet directed toward the elongated delivery member and configured to dispense a cleaning liquid at least onto a surface of the tip of the elongated delivery member; and
   a cleaning chamber comprising a passage for receiving the elongated delivery member therein with the tip of the elongated delivery member being positioned in the delivery position at a spaced distance from inner surfaces of the chamber, wherein the at least one cleaning liquid distribution conduit leads to the chamber interior, wherein the cleaning distribution conduit comprises at least one nozzle configured for delivering a spray of cleaning liquid in a diffuse manner so that the cleaning liquid also impacts on inner surfaces of the chamber and wherein the nozzle includes one or more slits or restrictions configured to dispense a cleaning liquid spray.

13. A food liquid package comprising:
   a container with liquid food and a tube connected by one end to the container and by an other end to a connection fitment of a hygienic liquid food delivery device for dispensing the liquid food to or from a food or beverage dispenser, the delivery device comprising:
      at least one elongated delivery member for connecting to a liquid food source, the elongated member being tubular to duct the liquid food to an outlet at a tip of the delivery member, the outlet being configured for dispensing the liquid food to or from the dispenser with the outlet of the elongated delivery member being positionable in a delivery position at a distance of all surfaces of the dispenser;
      at least one cleaning liquid distribution conduit with at least one outlet directed toward the elongated delivery member and configured to dispense a cleaning liquid at least onto the surface of a tip of the elongated delivery member; and
      a cleaning chamber comprising a passage for receiving the elongated delivery member therein with the tip of the elongated delivery member being positioned in the delivery position at a spaced distance from inner surfaces of the chamber, wherein the elongated delivery member is a part of a connection fitment comprising a body with a liquid inlet for receiving the food liquid; with the connection fitment being configured to connect to the cleaning chamber.

14. A hygienic liquid food delivery device for dispensing a liquid food to or from a food or beverage dispenser, the delivery device comprising:
   at least one elongated delivery member for connecting to a liquid food source, the elongated member being tubular to duct the liquid food to an outlet at a tip of the delivery member, the outlet being configured for dispensing the liquid food to or from the dispenser with the outlet of the elongated delivery member being positionable in a delivery position at a distance of all surfaces of the dispenser, wherein the elongated delivery member is a hollow needle that is protected by a protective member attached to the body to keep the needle clean before a first use and wherein the protective member comprises a collapsible portion which surrounds the needle and a septum that is attached to said portion; and
   at least one cleaning liquid distribution conduit with at least one outlet directed toward the elongated delivery member and configured to dispense a cleaning liquid at least onto a surface of the tip of the elongated delivery member.

15. The device according to claim 14, wherein the collapsible portion of the protective member is configured to collapse as the needle is inserted in the chamber to allow the needle to puncture the septum to uncover at least the outlet of the needle in the chamber.

16. The device according to claim 14, wherein the protective member is attached to a body of a fitment by a ring snapped on a circumferential edge of the body.

17. A hygienic liquid food delivery device for dispensing a liquid food to or from a food or beverage dispenser, the delivery device comprising:
   at least one elongated delivery member for connecting to a liquid food source, the elongated member being tubular to duct the liquid food to an outlet at a tip of the delivery member, the outlet being configured for dispensing the liquid food to or from the dispenser with the outlet of the elongated delivery member being positionable in a delivery position at a distance of all surfaces of the dispenser, wherein the elongated delivery member is a hollow needle that is protected by a protective member attached to the body to keep the needle clean before a first use; and at least one cleaning liquid distribution conduit with at least one outlet directed toward the elongated delivery member and configured to dispense a cleaning liquid at least onto a surface of the tip of the elongated delivery member, wherein a connection fitment is further protected by a tamper evidence cover which overlaps the protective member.

* * * * *